(12) United States Patent
Hu (10) Patent No.: US 7,829,302 B2
(45) Date of Patent: Nov. 9, 2010

(54) METHOD FOR DETECTING THE SPECIFICITY OF ACTIVATED LYMPHOCYTE

(76) Inventor: Jun Hu, 352-26-3.17 Chang Le West Road, Xi'an Shanxi (CN) 710032

( * ) Notice: Subject to any disclaimer, the term of this patent is extended or adjusted under 35 U.S.C. 154(b) by 888 days.

(21) Appl. No.: 10/582,056

(22) PCT Filed: Dec. 7, 2004

(86) PCT No.: PCT/CN2004/001427

§ 371 (c)(1), (2), (4) Date: Jan. 29, 2007

(87) PCT Pub. No.: WO2005/083427

PCT Pub. Date: Sep. 9, 2005

(65) Prior Publication Data

US 2007/0172448 A1 Jul. 26, 2007

(30) Foreign Application Priority Data

Dec. 8, 2003 (CN) .................. 2003 1 0119872

(51) Int. Cl.
*G01N 33/53* (2006.01)
*G01N 33/567* (2006.01)

(52) U.S. Cl. .................. 435/7.24; 435/5; 435/7.32

(58) Field of Classification Search .................. None
See application file for complete search history.

(56) References Cited

U.S. PATENT DOCUMENTS

| 5,801,144 | A | * | 9/1998 | Karpas et al. ............... 514/11 |
| 6,150,121 | A | * | 11/2000 | Hamawy et al. ............ 435/7.24 |
| 6,346,247 | B1 | * | 2/2002 | Stafford et al. ............ 424/158.1 |
| 7,659,084 | B2 | * | 2/2010 | Frentsch et al. ............ 435/7.24 |
| 2003/0211548 | A1 | | 11/2003 | Packard et al. |

FOREIGN PATENT DOCUMENTS

| CN | 1112933 A | 12/1995 |
| CN | 1444043 A | 9/2003 |
| EP | 0 289 896 A1 | 11/1988 |
| WO | WO 03/044529 A1 | 5/2003 |

OTHER PUBLICATIONS

Bach, F. et al. 1964 "Lymphocyte interaction: a potential histocompatibility test in vitro" *Science* 143:813-814.

Birkeland, S.A. 1976 "Immunological follow-up of 41 renal allograft recipients" *Scandinavian J. Urol. Nephrol.* Supplementum 31: 5-37.
Cullen, P.R. et al. 1977 "Mixed lymphocyte reaction and graft survival in forty cadaveric renal transplants" *Clin. Exp. Immunol.* 28:218-222.
Hartono, C. et al. 2004 "Noninvasive diagnosis of acute rejection of solid organ transplants" *Frontiers in Bioscience* 9:145-153.
Hu, J. et al. 2006 "Suppressive effects of antigens on the activity of specific activated lymphocytes: a test to define the specificity of activated lymphocytes" *J. Medical Colleges of PLA* 21:169-177.
Lenardo, M. et al. 1999 "Mature T lymphocyte apoptosis—immune regulation in a dynamic and unpredictable antigenic environment" *Annu. Rev. Immunol.* 17:221-253.
Migliaccio, M. et al. 2006 "Distinct mechanisms control human naïve and antigen-experienced CD8+ T lymphocyte proliferation" *J. Immunology* 176:2173-2182.
Sampson, D. et al. 1976 "Immunological responses in identical twins with renal transplants from a common donor" *The American Surgeon* 42:572-578.
Seki, Y. 1983 "Analysis of specific cellular immunity in renal transplant recipients by MLR & CML" *Nippon Geka Gakkai Zasshi* 84:488-499. Abstr. only in English.
Sengar, D.P.S. et al. 1976 "Development of specific nonreactivity in human cadaveric renal allograft recipients" *Tissue Antigens* 7:281-290.
Sheehy, M. et al. 1975 "HL-A LD (lymphocyte defined) typing: a rapid assay with primed lymphocytes" *Science* 188:1308-1310.
Steinmann, J. et al. 1994 "Failure of in vitro T-cell assays to predict clinical outcome after human kidney transplantation" *J. Clinical Lab. Analysis* 8:157-162.
Svejgaard, A. et al. 1975 "Developments in histocompatibility testing" *Analysis Transplantation Nephrology*, Eds. Moorhead et al. 12:121-128.

* cited by examiner

*Primary Examiner*—David A Saunders
(74) *Attorney, Agent, or Firm*—Knobbe Martens Olson & Bear LLP (57) ABSTRACT

A method for detecting the specificity of activated lymphocytes is provided. The present method can be used to detect the specificity of activated lymphocytes in recipients or patients after organ transplantation or being infected by pathogenic microorganism or vaccination. The establishment of the present invention can not only timely diagnose rejection in organ transplantation, but also provide guidance for rational medicament administration clinically. Furthermore, the present invention provides an accurate and quick method to detect infectious diseases. It will be significant to achieve the goals of early detection, early quarantine, early treatment, thereby reducing infection rate.

9 Claims, 4 Drawing Sheets

METHOD FOR DETECTING THE SPECIFICITY OF ACTIVATED LYMPHOCYTE

RELATED APPLICATIONS

This application is a U.S. National Phase of International Patent Application No. PCT/CN2004/001427, filed Dec. 7, 2004, designating the U.S. and published not in English on Sep. 9, 2005 as WO 2005/083427, which claims the benefit of Chinese Patent application No. 200310119872.1, filed Dec. 8, 2003.

BACKGROUND OF THE INVENTION

1. Field of the Invention

The present invention relates generally to a method for detecting the specificity of activated lymphocyte. More particularly, the present invention relates to a method for detecting the specificity of activated lymphocyte in vivo after transplantation, virus/bacteria infection, or vaccination.

2. Description of the Prior Art

Immune or immunity is a physiological response for biological recognition and clearance of foreign antigens (pathogens). Most antigens are not autologous, but from exogenous sources (foreign antigen). After entering the body, foreign antigens will be recognized and eliminated promptly through a series of immune responses initiated by the immune system of the body.

During transplantation, the antigenicity differences between donor and recipient, such as the differences between major histocompatibility antigen (MHC) and Minor histocompatibility antigen (mH-antigen), can induce the recipient to produce specific activated lymphocytes targeting antigens, which are present in the organ/tissue from donor and are different from those antigens from recipient. The lymphocytes thus produced will then attack the organ being transplanted, resulting in rejection reaction. Specific activated lymphocytes targeting different pathogens can also be produced when body is stimulated/infected by pathogenic microorganisms such as measles virus, respiratory syncytial virus, hepatitis A virus, hepatitis B virus, hepatitis C virus, hepatitis E and F virus, chickenpox and herpes zoster virus, herpes simplex virus, cytomegalovirus, EB virus, coronavirus, rotavirus, Coxsackie virus, ECHO virus, Ebola virus, Yellow fever virus, Adenovirus, forest encephalitis, Rubella virus, Dengue fever virus, epidemic encephalitis B virus, Rabies virus, SARS virus, Influenza virus (include human and birds), epidemic mumps virus, hemorrhagic fever virus, HIV, poliomyelitis virus, *Rickettsia*, epidemic encephalitis diplococcus, *Bacillus typhi* or *Bacillus paratyphosus*, *Mycobacterium tuberculosis*, *Bacillus diphtheriae*, *Bordetella pertussis*, *Bacillus anthracis*, *Bacterium burgeri*, *Yersinia pestis*, *Lepra bacillus*, atypical *Mycobacterium*, *Leptospire*, *Treponema pallidum*, *Spirochaeta recurrentis*, *Chlamydia*, *Cyptozoite*, *Leishmania*, *Toxoplasma*, *Schistosome*, *Paragonimiasis*, Chinese liver fluke, *Fasciolopsis*, *Filaria*, etc. A variety of specific activated lymphocytes targeting various antigens can exit in the same body, for instance, to a patient who suffered rejection and was infected by herpes virus after heart transplantation, his body will generate both specific activated lymphocytes against MHC and mH-antigen of the donor organ and specific activated lymphocytes against herpes virus.

Transplantation is the last hope in the end-stage treatment selections for many organs. After transplantation, the differences in MHC and mH-antigen between donor and recipient always give rise to rejection, which remains a major cause of mortality at 3, 5, and 10 years after organ transplantation such as heart, liver, kidney and marrow transplantation, as well as cellular transplantation, and rejection starts from lymphocytes activation. The presence of anti-donor specific activated lymphocytes in the recipient generally indicates body has initiated or is initiating attacks on donor organ. Accordingly, appropriate measure, such as increasing the dosage of the immunosuppressive agent used or changing to another type of immunosuppressive agent, should be adopted promptly to make the transplanted organ function normally in the recipient, so as to improve the life quality and life span of the recipient.

Biopsy, which is an invasive method and can not be repeated daily, is the current golden standard for rejection diagnosis worldwide. This method, however, has not been widely accepted by doctors and patients because it causes painful experience, and it is dangerous and expensive. Furthermore, because foci severities only exit in certain parts of an organ, and biopsy sample can be only taken from a certain part of the organ, the misdiagnosis rate can be high; In addition, the purpose of biopsy is to detect pathological changes, thus, the discovery of pathological changes actually indicates organ has been damaged already. Therefore, what is needed is to provide a non-invasive diagnostic method, which is fast, convenient, and has high sensitivities to rejection reaction to improve the life quality of organ recipient and the life span of the organ transplanted. Rejection starts as the activation of lymphocytes, therefore, activated lymphocytes should exist prior to pathological changes. Accordingly, the present invention is designed to diagnose rejection reaction through the detection of specific lymphocytes activated by MHC or mH antigen in peripheral blood. As a result, the method provided in the present invention can diagnose rejection reaction well before pathological changes occur in transplanted organ. Additionally, the method provided herein is easy to carry out, easy to be standardized, and can be converted to automatic operation. Moreover, the method can overcome the defects in biopsy assay and provide quick, accurate and definite diagnostic result for rejection reactions. The method can be used as a guidance for dose usage of immunosuppressive agent in clinic. The method can also be used to improve the life quality of patients and extend the life span of implant.

Many pathogenic microorganisms such as measles virus, chickenpox virus, epidemic encephalitis B virus, and *Mycobacterium tuberculosis* etc. have a latent period before occurrence of diseases, during which the symptoms are generally atypical such as fever etc. The diagnosis of the diseases caused by these pathogens, however, generally depends on the diagnosis of typical symptoms (specific symptoms), the occurrence of which is always delayed in such diseases due to the latent period. As a result, the misdiagnosis rate can be high.

The present invention can also be used to diagnose the infection of pathogenic microorganism. It provides an accurate and quick method to detect diseases in the latent period and early stage. Accordingly, it will be significant to realize the goals of early to detect, early to quarantine, early to treat, and reducing infection rate.

DETAILED DESCRIPTION OF THE INVENTION

The present invention related to a method for detecting the specificity of activated lymphocytes, comprising the steps of:

1) diluting antigen sample by medium, wherein the antigen can activate lymphocytes in body, and wherein the medium contains, in addition to regular ingredients of cell culture, neutralizing antibodies against cytokines which induce cell proliferation, and/or cytokines which induce mononuclear cell apoptosis or inhibit cell activation or inhibit cell proliferation;

2) preparing mononuclear cell suspension with the medium, wherein the suspension contains activated lymphocytes;

3) incubating mixture of the antigen and the above mononuclear cell suspension containing the activated lymphocyte on cell culture plate;

4) determining the existence of antigen-specific activated lymphocyte by comparing the differences of detectable signals between test wells and control wells.

In one aspect, the present method can be used to detect the specificity of the activated lymphocytes produced by the body being stimulated by any antigen.

In another aspect, the antigen used in the present invention can be allogeneic antigens, heteroantigens, or antigens from different types of pathogenic microorganism. Allogeneic antigens and heteroantigens sample can be a single antigen or can be mixed antigens from one or more individuals. The antigens can be provided in the form of particulate antigen existing on cell membranes of human or animal cells, or cell membranes or cell walls of molds and bacteria, or envelops or capsids of viruses. The antigen(s) can be also provided as soluble antigens dissolved in solutions.

In one aspect, allogeneic antigens can be the direct or indirect product of alleles, which can be recognized as an antigen by another member of the same species. The products of the alleles include not only polypeptide, but also specific polysaccharides and lipids synthesized by enzymes encoded by the alleles. The allogeneic antigens used in the present invention are histocompatibility antigen, including major histocompatibility antigen (MHC) (also known as "HLA" in human, "SLA" in swine, "MAMU" in monkey, "PYCY" in yellow baboon, $H_2$ antigen in mice, $RT_1$ antigen in rat) and minor histocompatibility antigen (mH-antigen).

Heteroantigens, as used herein, refer to substances (e.g. polypeptide, specific polysaccharides, lipids etc) that exist in one but not in the other of two species. It can be recognized by the other species and therefore can induce immune response. For instance, if an organ from swine is going to be transplanted to human, monkey, baboon, or chimpanzee etc, the substances (as previously described) existing in the swine but not in the bodies of human, monkey, baboon, or chimpanzee etc are called heteroantigens.

In one aspect, the pathogenic microorganism antigen is a specific antigen of a bacterium or virus. Alternatively, the pathogenic microorganism antigen is antigen mixture from bacteria and/or viruses (each bacterium or virus can express many types of antigen). It can be provided as a formulation prepared by treating bacterium or virus particulate with non-ion abstergent and lipid solvent or 10% formaldehyde. The antigens from bacterium or virus can also be expressed on the cell membranes of human/animal cells. The antigens can also be provided in the form of soluble antigen dissolved in solutions.

As used herein, "target antigen(s)" refers to antigens which are used in the assay and their specific activated lymphocytes may have existed in subjects, and which can be identified by the assay.

As used herein, "irrelevant antigen(s)" refers to antigens, which are used as controls in the assay and their specific activated lymphocytes must not have existed in subjects. Irrelevant antigens can be different according to the purposes of the assays. Irrelevant antigens can be added in the assay additionally, or, they can be added into the same pick-up plate as controls each other.

The antigen(s) used in the present invention can be particulate antigens, such as human HLA antigen(s) carried by cells, bacteria or viruses; or virus antigen or bacteria antigen carried by a certain cell, bacterium or virus. Alternatively, the antigens can be soluble antigens such as allogeneic antigen molecules or heteroantigen molecules or some specific protein molecules from certain virus or bacterium.

The antigen(s) used in the present invention can be a single type of allogeneic or heteroantigen molecules, it can also be a mixture containing several or entire human HLA and mH antigens. The antigen(s) can also be a single type of specific antigen from virus or bacterium. The antigen(s) can further be mixed antigens from a variety of viruses or bacteria. Using single antigen or using mixed antigens can result in different accuracies. For example, when mixed allogeneic antigen are used in the assay, a positive result can only means there exists allogeneic antigen activated lymphocyte, i.e., the immune system of the body has initiated rejection reaction against donor organ, but one will not know exactly which antigen molecule actually induced the rejection reaction. By using a pick-up plate separating different HLA and mH antigens into individual compartment/well, however, a positive result can indicate exactly the activated lymphocytes were actually activated by which one or several allogeneic antigen(s). Likewise to the diagnosis of virus or bacterium infectious disease, if mixed antigens from respiratory syncytial virus, coronavirus, adenovirus, influenza virus and parainfluenza virus, measles virus, chickenpox virus, mumps virus, herpes virus etc. are used in the assay, a positive result can only indicate that the subject is infected by one of the aforesaid pathogens, but no way to indicate which is the one to blame. In contrast, if a single specific protein of a certain virus or a relatively single type of a certain virus specific protein is used as antigen in the assay, one can establish which virus is the pathogenesis based on test result.

The antigen(s) in the present invention can be prepared from the following method:

1. Specific recipients (the HLA antigens of each recipient are mostly different) were chosen to allow them to possess, on the membranes of B cells in peripheral blood, the entire human HLA-I antigens, HLA-II antigens, and mH antigens thereof. Different combination is formed naturally in different individual, and we can make choices according to our needs only. A 0.5 ml peripheral blood sample was taken from each subject and placed into culture bottle containing appropriate amount of cell culture medium, e.g. 1640 medium (GIBCO company), DMEM (GIBCO company) or Eagle (GIBCO company) medium comprising 10% calf serum or fetal calf serum (GIBCO company)). At the same time, appropriate amount of supernatant of cultured B958 cell strain (commercially available from ATCC company), which can secret EB virus into the cell culture medium during incubation was added. The amount of the supernatant should contain enough EB virus to transform all B cells in the 0.5 ml blood (typically, 5-10 ml supernatant of B958 cell culture suspension which has been incubated for 3 days and the original concentration of the cell is 500,000 B958 cell per ml). The cell culture bottle was then placed into $CO_2$ incubator under 37° C. for about 15 days (during which 5-10 ml medium was added every 5 days) until aggregated tumor cells emerge in the suspension. After aggregated tumor cells appeared, the medium can be changed and the cells can be cultured in the same way as those in other regular cell cultures, except all utensils that have made contact directly or indirectly with B958 cell strain must been strictly sterilized to eliminate EB virus (Though EB exists ubiquitously, even in cavum nasopharyngeum of a health person, sterilizing procedure is still necessary). Peripheral blood from the subjects thus treated now can be used to set up different B cell strain thereof. After being cloned, amplified, and frozen, B cell strains thereof, which can stably express certain types of HLA antigens and/or mH antigens have been established.

2. Cell strains comprising human HLA and mH antigen can also be prepared according to the method of genetic engineering: human cell strains which do not express human HLA and/or mH antigen such as U937 (commercially available from ATCC company) and K562 (commercially available from ATCC company) were chosen and used as antigen vectors. Routine techniques in molecular biology were used to obtain mRNAs of white blood cells from peripheral blood of subjects. Routine techniques in genetic engineering such as reverse transcription PCR amplification, splicing, etc. can be used to establish expression vectors which can express different kinds of HLA antigen. These vectors were then transfected into U937, K562, or other cells, which originally do not express human HLA and mH antigen, to establish cell strains, which can express different types of HLA antigen individually, i.e. all human HLA antigens. The expression vectors can be selected from different retroviruses. The expression vectors can also be prepared by the methods described in *Immunogenetics* (25:1-6, 1987) etc. The methods can also be used to express the antigens. Different cell strains can be established respectively for each HLA antigen so that each cell strain can express one HLA antigen. By establishing more than 100 cell strains, all human HLA antigens are included therein. After being cloned, amplified, and frozen, cell strains, which can stably express certain human HLA antigens or mH antigens, would be established, respectively.

3. Cell strains comprising human HLA and mH antigen can also be prepared according to the following method:

3.1 Human cell strains, which are known to either express or do not express human HLA and/or mH antigen, such as Raji (commercially available from ATCC company), U937 (commercially available from ATCC company), K562 (commercially available from ATCC company), and mice ascites tumor cell strain SP2/0 were chosen and used as tumor cell strains. B cells containing known HLA antigen(s) in peripheral blood were chosen (Abe et al. *J. Immunol. Methods*, 90:111-123; "Principles and techniques of culture in vitro", (Xue Qingshan, Science Publishing House, 2001, edition 1); "*Selected Methods In Celluar Immunology*" (Edited by Barbara B. Mishell and Stanley M. Shiigi. W. H. Freeman and Company, San Francisco, 1980); and "Concise Immunology Techniques" (Zhu Zhengmei and Liu Hui, Science Publishing House, July 2002, edition 1), then bacteria lipopolysaccharide (LPS) (SIGMA) was added until its final concentration is 2-25 μg/ml. A mixture of B cell growth factor (BCGF) (self-made, see 3.2), anti-human IgM (Sigma company), pokeweed (PWM) (Sigma company) (final concentration is 1-25 μg/ml) and *Staphylococcus* A protein (Sigma company) (final concentration of 1/1000-1/10000) were co-incubated for 2-3 weeks. Then, Raji, U937 or K562U cells was fused with human mononuclear cells with known antigen which had been stimulated by the mixture of B cell growth factor (BCGF), anti-human IgM, *Staphylococcus* A protein, bacteria lipopolysaccharide, and pokeweed (PWM) for 2-3 weeks to obtain immortalized cell strain which can express certain kind(s) of HLA antigen by the technique described in "Techniques of Monoclonal Antibody" (Xu Zhikai edited, Science and Technology Publishing House in Shaanxi Province, China January, 1992, edition 1). Thus, cell strains that can express different combinations of HLA antigens were established. Thereby, a variety of cell strains were established to contain almost all human HLA antigens.

3.2 Establishment of B cell strain: see "Principles and techniques of culture in vitro" (Xue Qingshan, Science Publishing House, 2001, edition 1).

1). Preparation of lymphocyte: Drew peripheral blood from patient with known HLA antigens, added heparin to anticoagulate (Sigma company), isolated mononuclear cells by using lymphocyte isolation solution (Sigma company), made cell suspension (concentration: $1\times10^6$ cell/ml) with RPMI 1640 medium (GIBCO company) containing 10% FCS, incubated the cells in the cell culture bottle for 4-8 hours, shook the bottle to make the cells suspended, centrifuged the suspension for 10 min at 1,000 r/min and collected the precipitates, which are purified lymphocytes.

2). Preparation of supernatant of cultured BCGF: Made lymphocyte suspension (concentration: $2\times10^6$ cell/ml) with RPMI 1640 medium (GIBCO company) containing 1% FCS (GIBCO company), added PHA into the suspension to a final concentration of 2 pg/ml, placed the suspension into the culture bottle, incubated the bottle in a incubator with saturated humidity and 5% $CO_2$ at 37° C. for 3-4 days, collected the culture into a centrifuge tube, centrifuged the culture for 10 min at 1,500 r/min under 4°X, collected the supernatant and stored it under −20° C. The supernatant is raw BCGF.

3). Made lymphocyte suspension (concentration: $1\times10^6$ cells/ml) with RPMI 1640 medium (GIBCO company) containing 10% FCS, added anti-human IgM $F(ab)_2$ fragment (Sigma company) into the suspension to a final concentration of 20 μg/ml, added the raw BCGF into the suspension to a final concentration of 10%, and added bacteria lipopolysaccharide (LPS)(SIGMA) into the suspension to a final concentration of 2-25 μg/ml.

4). A 1 ml cell suspension was added into each well of a 24-well plate. Cells were incubated in $CO_2$ incubator at 37° C. Half culture medium was renewed every 3-4 days, i.e., removing 0.5 ml suspension from the wells and then adding new culture medium containing anti-human IgM $F(ab)_2$ fragment (Sigma company) (20 μg/ml), raw BCGF (10%), and bacteria lipopolysaccharide (LPS)(SIGMA) (final concentration of 2-25 μg/ml). 3-5 weeks later, when clones grew bigger, the cells were transferred into a culture bottle and continue to culture. B cell strain with known HLA antigens were then established.

5). Thus, cell strains that can express different combinations of HLA antigens were established. A variety of cell strains were established to contain almost all human HLA antigens.

4. Cell strains containing human HLA antigen and mH antigen can also be obtained through the following method: person who does not share the same HLA antigens with others or who shares very few types of HLA antigens with others were chosen as subjects. Peripheral blood was drawn from these persons; B cell strains thereof were established according to method 1; these cell strains were used as vectors and genetic engineering method (as described in method 2) were used to express those HLA antigens and mH antigens which can not be expressed by the cell strains. As such, one can use less cell strains to express more antigens, thus can express all human HLA antigens and mH antigens with minimal cell strains. According to this strategy, only several cell strains are needed to be established to express all 18 DR antigens having been discovered so far in human on cell surface, when using Raji cell strain (commercially available from ATCC company) or Daudi cell strain (commercially available from ATCC company) which can express more HLA-II antigens as antigen vectors.

5. Cells or cell strains (expressing all human HLA antigens) obtained through methods described above or through other methods such as obtaining directly from human or animal spleens/peripheral blood were cultured and amplified. Then, the cells were mixed and broken down by using sterilized distilled water and incubating at 37° C. for 0.5-2 hours. When cells were broken down completely, refrigerated high-speed centrifuge (3,000-20,000 g) was used to precipitate cell membrane for 20 minutes. The supernatant was removed, and the precipitate (cell membrane) was frozen-dried and stored for use. When being used, the precipitate will be diluted by cell culture medium to obtain single or mixed HLA particulate antigen, and the diluted concentration is different depending on purpose. In fact, the HLA particulate antigen has been carried on the lipid body.

6. The HLA antigens used in the present invention can also be soluble antigens. The soluble antigens can be obtained by method as follows: Vectors constructed by method 2 can express HLA antigens in human cells, prokaryotic cells, or other eukaryotic cells (such as yeast). The HLA antigens thus obtained, no matter in which approach, can be used directly as antigens after being fixed in 10% formaldehyde and washed. Alternatively, purified HLA antigens can be obtained by routine affinity chromatography (such as affinity column prepared by anti-B2 microglobulin antibody (provided by Forth Military Medical University) or anti-HLA type I or type II antigen antibody (provided by Forth Military Medical University)) or other protein purifying techniques). The purified HLA antigen thus obtained can be used in further experimental uses.

7. Preparation of pathogenic microorganism specific antigen: The preparations of various pathogens such as measles virus, chickenpox virus, and *Mycobacterium tuberculosis* can refer to references such as "Principles and Techniques of Culture in vitro" (Xue Qingshan, Science Publishing House, 2001, edition 1); "Diagnosis and Experimental Virology" (Zhengzhou University Publishing House, 2002, edition 1, edited by Yang Zhanqiu, Liu Jianjun, Xiao hong, Ding Xiaohua); "Experimental Virology in Medical Use" (Du Ping. Chinese PLA Medical Publishing House, 1985, edition 1); "Modern Pathophysiology" (Chinese PLA Medical Publishing House, 2000, edition 1, edited by Zhang Dunrong), etc. The pathogenic microorganisms were cultured in vivo or in vitro according to their growth and re productive characters, and were purified using respective method. The purified or relatively purified pathogens can be used as antigens after further treated by $^{60}C_o$ irradiation and inactivated by 0.4-40 g/L formaldehyde, glutaraldehyde, non-ion detergent or lipid solvent (such as diethyl ether, chloroform) treatment. The specific antigens of the pathogenic microorganisms can also be specific antigens of the microorganisms expressed by using genetic engineering methods. These antigens can be expressed in human or animal cells, prokaryotic cells, or eukaryotic cells. These cells can be directly used as antigens. Alternatively, these cells can be used as antigens after purified by routine affinity chromatography or other protein purifying techniques.

8. The antigens used in the present invention can also be heteroantigens for heterogenic transplantation, such as antigen from donor swine (including all kinds of transgenic swine, and inbred line), or mice antigen, rat antigen, guinea pig antigen etc. Different cell strains can be set up to express above antigens, which can be used as antigens to be tested during heterogenic transplantation.

9. The antigens in the present invention can be made in laboratory, or can be commercially purchased from companies. Antigens from measles virus, epidemic encephalitis B virus, poliomyelitis virus, *bacillus* diphtheriae, for instance, are commercially available.

A wide range of antigens can be used in the present invention, including all "foreign" substances, which can specifically activate lymphocytes in body. As such, the antigens can be used to detect the existence of specific lymphocytes activated by the antigens.

All antigens obtained by above or other methods (including singular or mixed antigens, particulate antigens or soluble antigens, allogeneic or heteroantigens, human HLA antigen or antigens from mouse, rat, swine etc, antigens from pathogenic microorganisms such as bacterium and virus, as well as all kinds of vaccine antigens for human use), as long as they can specifically activate lymphocytes in body, can be used to detect the existence of specific lymphocytes activated by the antigens.

The antigens obtained which can be expressed on human or animal cells, bacterium cell wall or envelop/capsid of virus, need to be inactivated by mitomycin or by 0.1-10% formaldehyde or non-ion detergent as well as lipid solvent (such as acetone, dimethyl benzene, chloroform etc.) treatment before it can be used as test antigen sample. Under certain circumstances, the antigens can be directly used as test antigen sample without further treatment. Protein antigens (soluble antigens) purified by affinity chromatography or other protein purifying methods, and target antigens absorbed on liposome can be directly used as test antigens.

The antigens obtained through sterile operation can be used separately or with different combinations (according to different purposes). The antigens were incubated with peripheral blood mononuclear cells from subjects, obtained through methods using routine lymphocyte separation medium to prepare mononuclear cells. The medium used to dilute mononuclear cells contains, in addition to calf or fetal bovine serum required in routine cell culturing (commercialized serum-free medium can also be used), cytokine activity neutralizing antibody, and/or cell proliferation inhibitory cytokine, and immunosuppressive agent and/or anticancer medicaments. The immunosuppressive agent and/or anticancer medicaments include Prograf (FK506), Cyclosporin such as Cyclosporin A, Cyclosporin C, cyclophosphamide, azathioprine, rapamycin, RS-61443 (mycophenolate mofetil, MM, molecular formula: $C_{24}H_{11}NCLO_7$)(which is an ester derivative of mycophenolic acid, MPA, molecular formula $C_{17}H_{11}O_6$), BQR(6-fluo-2-3 methyl-4-quinolinic acid), deoxyspergualin, immunosuppressant secreted by human acute T lymphocytic leukemia cell strain JM, adrenal cortex hormone (such as medrat, prednisone, hydrocortisone, dexamethasone, etc.), topoisomerase inhibitor (such as camptothecin (CAM), etoposide (VP-16), alkyling agent (such as cisplatin, caryolysine, alkeran, Chlorambucil, carmustine, etc.)), antimetabolite (methotrexate, cytosine arabinoside, thymidylate synthetase inhibitor, dinitrogen tetrahydrofolic acid, etc.), derivatives of retinoic acids-vitamin A (such as all-trans retinoic acid, palmitate xanthopsin, 4-N-hydroxybenzene retinoic-ammonia), and other medicaments which are potentially capable of inducing immunosuppressive function or inducing tumor apoptosis. The function of the antigens mentioned above is to suppress the activation of specific activated lymphocytes targeting the antigens or induce active apoptosis of the specific activated lymphocytes targeting the antigens; the function of cytokine activity neutralizing antibody and/or cell proliferation inhibitory cytokine is to induce passive apoptosis of the activated lymphocytes; the function of the immunosuppressive medicaments aforesaid is to make the test result more stable, accurate, sensitive, and easy to compare with controls.

The dosages or concentrations of the immunosuppressive agents and anti-cancer medicaments in the culture medium can be different. The concentrations or dosages can be adjusted as desired. Generally, the concentration is about 1000 times of the lowest medicament maintenance concentration (bottom value) in blood described in instruction manual (the dosage range is approximately 0.001 ng-100 µg/ml), for example, the dosage range of FK506 is 0.001 ng-10 µg/ml (preferably, 0.01 ng-100 ng/ml); cyclosporin A is 0.01 ng-10 µg/ml (preferably, 0.1 ng-1 µg/ml). The optimum concentration is the lowest concentration of the medicament, which can achieve best repetitiveness of test result. The immunosuppressive agents and anti-cancer medicaments can be used separately or in combination, according to different purposes.

The neutralizing antibodies of the cytokines which can stimulate cell proliferation include interleukin 1, 2, 3, 4, 5, 6, 7, 8, 9, 11, 12, 13, 14, 15, 16, 17, 18, 19, 20, 21, 22, and 23, interferon (-α, β, w, γ), granulocyte colony-stimulating factor (G-CSF), macrophage colony stimulating factor (M-CSF), granulocyte-macrophage colony stimulating factor (GM-CSF), stem cell factor (SCF), thrombopoietin (TPO), nerve growth factor (NGF), and all other neutralizing antibodies for cytokines which can promote the activation and proliferation of mononuclear cells; cytokines which can induce apoptosis or inhibit activation or proliferation of mononuclear cells (e.g., lymphocyte and monocyte) include IL-2, IL-4, IL-10, IL-15, transforming growth factor β(TGF-β), interferon γ, tumor necrosis factor (TNF), CTLA4, and other cytokines or cytokine fusion proteins, such as CTLA4.Ig (the fusion protein of cytotoxic T cell related antigen 4 (CTLA4) and Fc fragment of human immunoglobulin G (IgG)) etc.

Neutralizing antibody, as used herein, refers to antibodies having inhibitory effects on the biologic activities of cytokines. The neutralizing antibodies can inhibit the biologic activities of cytokines, which can otherwise activate or stimulate cell proliferation, thereby inhibiting the biological functions of the cytokines.

The function of the neutralizing antibodies and inhibitory cytokines is to facilitate the specific inhibition effect of specific antigen on specific activated lymphocytes, i.e. the combined effect of the specific antigen and the neutralizing antibodies and inhibitory cytokine can inhibit the activities of the antigen-specific activated lymphocytes and mononuclear cells. As different cytokine functions differently, and the active unit or titer of the cytokines or the neutralizing antibodies of the cytokine made by different companies can be different, the concentrations of the neutralizing antibodies in culture medium can be very different, with the concentration rage of 1 µg-10 mg/ml. The appropriate concentration should be the concentration which can achieve reproducible test results with high sensitivity. The concentrations of inhibitory cytokines are calculated as active unit thereof, with the final concentration range of 0.01-1000 active unit/ml (generally, 0.1-50 active unit/ml). The optimum concentration should be the concentration, which can achieve best sensitivity and accuracy in test results.

There are many kinds of immunosuppressive agent, cytokine activity-neutralizing antibody, and cytokines which can inhibit the activities of lymphocyte or monocytes. The mechanisms of functions thereof are complicated. One or more factors can be chosen and used alone or in combination during the test to achieve sensitive, accurate, and re productive result.

The target antigens, non-related control antigen, and mononuclear cells from the subjects isolated by lymphocyte separation medium (obtained by the methods described in examples 1, 2, and 3) were diluted by medium containing appropriate concentrations of immunosuppressive agent and anti-cancer medicaments, cytokine neutralizing antibody, and/or inhibitory cytokines to appropriate concentrations.

When using cells carrying target antigens as antigens, such as antigens obtained by methods 1, 2, 3 and 4, the concentration of the cells is approximately $0.001\text{-}10\times10^6$/ml, preferably about $1\text{-}2\times10^6$/ml; and the concentration of the mononuclear cells of the subject is approximately $0.1\text{-}5\times10^6$/ml, preferably about $1\text{-}3\times10^6$/ml. If the antigens are soluble and purified antigens, the concentration of the specific target antigen (nonspecific protein not included) is approximately 0.1 µg/ml-10 mg/ml. The working concentration of the antigens obtained through method 5 is about the membrane antigens of $0.1\text{-}100\times10^6$ cells per ml working solution. The antigens obtained through method 6 or 7 are generally considered as target antigens, with the concentration of the working solution of 0.1 µg-10 mg/ml.

The target antigens with appropriate concentration and non-related negative control antigens were respectively co-incubated with mononuclear cell sample to be tested in the wells of a cell culture plate. 100 µl antigens and 100 µl cells to be tested were added in each well, and then incubated in $CO_2$ incubator at 37° C. Under the cell culture environment provided by the present invention, the activity of activated lymphocytes was dramatically inhibited when the activated lymphocytes in the sample to be tested met specific antigens. After 3-72 hours of incubation, usually after 20 hours of the incubation, cell activities in test wells, non-related antigen control wells, and wells containing only mononuclear cells (without antigen) were tested. The existence of activated lymphocyte specific to known antigens can be determined by the activity changes in each well. There are two methods to test cell activities: direct method and indirect method. The former method adds certain substance directly into the wells, and the cell activity is evaluated by the ability of the cell to clean (the ability to prevent the substances such as tetrabromofluorescein, Trypan Blue and eosin from entering the cell) or convert (the ability of converting soluble MTT to formazans crystal) the substance, said ability can be used as a detectable signal; the latter method chooses appropriate detecting method and detectable signal according to the reaction principles of the present invention. For example, if the declination of cell activity is caused by cell apoptosis, then different evaluating methods for cell apoptosis can be used as detectable signals to determine cell activity changes in terms of the amount of apoptosis cells (see "Molecular Medicine of Apoptosis" (edited by Hu Ye, Ling Zhiqiang, Shan Xiaoyun, August, 2002, Military Medical Science Publishing House)).

Detectable signals as used herein means through a certain means or by adding certain substance(s) to make the reacting result of the mononuclear cell to be tested in test well visible to naked eyes or visible with the aid of observation devices, i.e. the displaying (demonstration) manners of the resultant changes of the mononuclear cells to be tested.

The detectable signals in the present invention mainly include:

1. MTT colorimetry: MTT was added to each well. The changes (increase or decrease) of cell activity can be found out by observing the amount of formazan crystal converted from soluble MTT by cells in different groups.

2. Cell staining method: See "Molecular Medicine of Apoptosis" (edited by Hu Ye, Ling Zhiqiang, Shan Xiaoyun, August, 2002, Military Medical Science Publishing House). According to the reaction principles provided by the book, cells were stained by hematoxylin-eosin stain, methyl green-pyronine stain, Giemsa stain, Wright's stain. Then the cells were observed under microscope. The ratio of cell apoptosis in every group was calculated according to the characteristics changes of apoptosis cells.

3. Fluorescent antigen staining method: See "Molecular Medicine of Apoptosis" (edited by Hu Ye, Ling Zhiqiang, Shan Xiaoyun, August, 2002, Military Medical Science Publishing House). According to the reaction principles provided by the book, cells in different group were marked/stained by acridine orange, Propidium Iodide, ethidium bromide, rhodamine 123, fluorescein isothiocyanate (marker antibody). Then the cells were observed under fluorescence microscope to find out the amount of apoptosis cells in each group according to the characteristics changes of the apoptosis cells.

4. Enzyme linked immunosorbent assay: See "Molecular Medicine of Apoptosis" (edited by Hu Ye, Ling Zhiqiang, Shan Xiaoyun, August, 2002, Military Medical Science Publishing House). According to the reaction principles provided by the book, using anti-histone antibody and anti-DNA antibody and using enzyme-linked immunoassay of cell apoptosis, the amount of apoptosis cells was calculated by detecting the amount of fractured single-strand or double-strand DNA caused by cell apoptosis.

The relationship between MTT and Cell apoptosis assay is: MTT method utilizes the ability of living cell of converting soluble MTT into purple-blue formazan crystal (dead cell does not have this ability). The more the living cells, the more the activities, and the more the amount of purple-blue formazan crystals converted from soluble MTT. The purpose of cell apoptosis assay, in contrast, is to detect the apoptosis cells, i.e. the amount of dead cells. The amount of living cells to be tested in each experiment is fixed. Therefore, that more dead cells also indicates there exist less living cells. As a result, the amount of purple-blue formazan crystals converted from soluble MTT becomes less, and vice versa.

Though a variety of methods can be used to convert the test result of the invention into different kind of detectable signals, MTT colorimetry is believed, after comparison, to be the most convenient and sensitive approach to display the test results. After cell culturing, 10-20 µl MTT (5 mg/ml) was added to each well. The cells were then incubated at 37° C. in $CO_2$ incubator for 0.5-6 h, generally 1-2 h. Inverted microscope was used to observe the amount of purple-blue formazan crystals converted from yellow soluble MTT. Alternatively, the supernatant can be removed from each well after cell culturing, and 100-150 µl dimethyl sulfoxide (DMSO) was then added into each well. The culture plate was gently shaken for 5 minutes to fully dissolve the purple-blue formazan crystals. The absorbency values of different wells were measured by microtiter plate spectrophotometer at a wavelength between 490 nm-590 nm with maximum absorbency. The wavelength is generally 550 nm. The differences between test well and negative control cell were compared to detect the existence of antigen specific activated lymphocyte for known target antigens. The negative control well in the present invention further included wells containing only cells to be tested (without adding any antigen).

The creativity of the present invention lies in the fact it sets up a new method which uses known antigens to detect the specific activated lymphocytes or used known specific activated lymphocytes to detect specific antigens. The preparations of different antigens and the approaches to obtain the antigens do not belong to the content of the present invention. Antigens, obtained by any approach or in any form, can be used in the experiment of the present invention and can achieve the corresponding results. Using different antigens only means the specificities of the activated lymphocyte to be tested are different. Using different antigens has no influence on the operation of the experiment, experimental result, as well as the determination of positive or negative. A variety of antigens can be used in the present invention, but only several examples will be provided hereunder to illustrate the experimental operation, the purpose and the significance of the invention. The method provided by herein is called activated lymphocyte specificity assay (ALSA). The control experiment of the present invention is mixed lymphocyte culture (MLC) (*Science* 143:813-814, 1964; *Blood*, 23(1):108-116, 1964).

The invention, together with other objects and advantages thereof, will be best understood by reference to the following description taken in conjunction with the accompanying drawings.

BRIEF DESCRIPTION OF THE DRAWINGS

4C); the two pictures on the right side are testing results from MLC experimental group (FIG. 4A) and control group (FIG. 4D).

EXAMPLES

The following examples are provided only for illustrating purpose. By no means will it limit the present invention in any way.

Example 1

Establishment of the Present Method

Activated lymphocytes were prepared by one-way mixed lymphocyte culture (MLC): The primed (responder) and stimulator lymphocytes were obtained from the peripheral blood of unrelated and healthy volunteers, respectively. The lymphocytes were obtained by isolating the peripheral blood thereof with commercialized separation solution. The stimulator cells (the HLA antigens expressed on their cell membranes were used to stimulate the activation (the activity of the cells increasing) or the apoptosis (the activity of the cells decreasing) of the reaction (responder) cells) were treated with 25 µg/ml mitomycin, followed by washing with normal saline. Then, part of them were used in cell culturing of primary one-way MLC (preparation of activated lymphocyte), and the others were preserved in frozen condition (−70° C.) by routine method for future use (for re-stimulating activated lymphocytes from primary MLC).

4 days after regular primary one-way MLC culturing, the cells were collected and used as the activated lymphocytes. These lymphocytes, after being washed once by serum-free 1640 medium, were reused as responder cells in the present invention as well as in control study. In the present invention and control study; the cells, which were preserved in frozen conditions and have been used in primary one-way mixed lymphocytes reaction were used as stimulator cells. The suspension of primed lymphocytes and stimulator cells were prepared with 10% FCS 1640 culture medium ($2 \times 10^6$ cell/ml). The concentration of purified IL-2 neutralizational monoclonal antibody (N-mAb) 5C9 is 8 mg/ml (commercially available from Department of Immunology, Forth Military Medical University, China). Both experiment and control experiment have treatment group and control group. Control experiment is actually the second time MLC; ALSA test is actually adding 15 µl N-mAb in the second time MLC test system.

ALSA Test Group:
  Group B, test group: 100 µl responder cells+100 µl stimulator cells+15 µl N-mAb;
  Group C, control group: 100 µl responder cells+100 µl 10% FCS 1640 culture medium+15 µl N-mAb MLC Test Group:
  Group A, test group: 100 µl responder cells+100 µl stimulator cells;
  Group D, control group: 100 µl responder cells+100 µl 10% FCS 1640 culture medium.

Cell culture plates were round-profile 96-well plate, each group including triplicate wells. 100 µl responder cells were seeded in each well. Additional 100 µl stimulator cells were added in the two test groups. In contrast, in the two control groups, 100 µl 10% FCS 1640 medium were added rather than stimulator cells. In ALSA test, 15 µl N-mAb were added in each well of two groups. The cells were cultured in 37° C. $CO_2$ incubator for 20-24 hours, then 10 µl MTT solution was added in each well and kept in the incubator for another hour. The result was observed with reverse microscope. Alternatively, the culture medium in each well was removed and 150 µl Dimethyl Sulphoxide was added in each well to dissolve the purple-blue crystals in the wells completely. Absorbance value at 550 nm in each well was measured with a microplate reader.

TABLE 1

The test results of three ALSA and MLC experiments with three pairs of stimulator cells and responder cells from 6 different individuals. The cells were cultured for 20 hours (MTT chromometry)

| | ALSA | | | MLC | | |
|---|---|---|---|---|---|---|
| Experiment | Group B Test group | Group C Control group | Inhibition rate (%) | Group A Test group | Group D Control group | Inhibition rate (%) |
| 1 | 0.339 | 0.433 | −22 | 0.744 | 0.667 | +12 |
| 2 | 0.261 | 0.470 | −44 | 0.640 | 0.540 | +19 |
| 3 | 0.240 | 0.588 | −41 | 0.706 | 0.732 | −4 |

Note:
each value in the test group and control group is the mean value of a group of triplicate wells; inhibition rate indicates the inhibitory degree of stimulator cell (HLA antigen) to specific activated lymphocyte targeting HLA antigen; methylprednisolone and the FK506 were added in each well of ALSA test, with the final concentrations of 5 µg/ml and 0.125 ng/ml respectively.
No immunosuppressive agent was used in MLC test.
Inhibitory rate = (mean value of triplicate wells in test group at A550 nm/mean value of triplicate wells in control group at A550 nm) × 100%, wherein "−" means inhibition. "+" means enhancing, and similarly hereafter.

In both ALSA test and MLC test, stimulator cells were added in the same amount of responder cells in test groups. According to the current immunological theory, activity of the cells in test group should increase dramatically in MLC test. At least the MTT converting ability of the cells in test group should not be lower than that in control group, which only contains responder cells. The result in Table 1, however, shows that MLC test result can be increased or decreased result rather than a stable one. In current immunology field, it has been widely negated to use MLC to detect specific activated lymphocyte (i.e., secondary MLC). That is to say, MLC method is not an appropriate method to detect the specificity of activated lymphocyte. However, in ALSA test, the cell activity in test group is much weaker than that in control group, which is totally contrary to the result should-be in MLC test. The positive result shows the inhibitory effect, i.e.

when lymphocytes which can be activated by test antigens exist in responder cells, the activity of the lymphocyte in test group is inhibited. As a result, the activity in test group is weaker than the activity in control group; as shown by the same test results of cells from different individuals, the method is reliable. Thus, though ALSA test, which was established by adding IL-2 neutralizing monoclonal antibodies into MLC test system, is related to MLC test, ALSA test is actually a new method, which is totally different from MLC test, as shown by the different ingredients in the test system, different result, and different significance from MLC test. The purpose of using immunosuppressive agents is mainly to improve the sensitivity, stability and repeatability of test results. When allograft rejection is relatively strong, the inhibitory effects can be good even there was no immunosuppressive agent added (See Table 4 in Example 2).

Example 2

Use of the Method of the Present Invention for Diagnosing the Transplantation Rejection 1. Preparation of stimulator cells (used as cells containing HLA antigens to be tested): During heart transplantation, donor spleen was taken and grinded on 200 mesh net. The resultant spleen cells were washed twice by serum-free 1640 medium culture (GIBCO Company) at 1500 r/min. The supernatant was removed and the precipitate was prepared by serum-free 1640 medium culture into cell suspension with a concentration of $1 \times 10^8$ cells/ml. Routine human lymphocyte separation medium (GIBCO Company) was used to prepare mononuclear cells. The cells were centrifuged for 20 minutes at 2000 r/min in a horizontal centrifuge. The cells on the interface between the separation solution and 1640 medium were then removed and placed into another asepsis centrifuge tube. The cells were washed twice by serum-free 1640 medium at 1500 r/min and 1000 r/min, respectively. The supernatant was then removed (if red blood cells exist, the cells should be suspended in 37-40° C. 0.83% $NH_4Cl$ solution, then placed in 37-40° C. water bath for 10 minutes, and finally washed twice by serum-free 1640 medium at 1000 r/min.) and the precipitate was prepared by serum-free 1640 medium containing 25 µg/ml mitomycin (Sigma company) into cell suspension with a concentration of $1 \times 10^7$ cells/ml. The cells were placed into 37° C. water bath for 40 minutes, then centrifuged at 1000 r/min for 10 minutes. The supernatant was removed and the precipitated cells were washed three times by serum-free 1640 medium at 1000 r/min. The precipitate was made into cell suspension with a concentration of $2 \times 10^7$ cells/ml by frozen-store solution (prepared according to "Practical Monoclonal Antibody Technology", edited by Xu Zhikai, ShaanXi Science and Technology Publishing House, 1992, edition 1). The cell suspensions were divided into frozen-store tubes and stored at –70° C. in refrigerator or liquid nitrogen for future use.

2. Purified IL-2 neutralizing monoclonal antibodies (produced by Department of Immunology, Fourth Military Medical University) were prepared with serum-free 1640 medium or PBS solution to 6 mg/ml. Disposable needles filter were used to filter bacteria. The solution was stored at –20° C. for future use. 5 mg/ml Tetrazolium (MTT, Sigma company) was prepared as working solution by normal saline. Disposable needles filter were used to filter bacteria from the working solution. The filtered solution was divided into tubes and stored at –20° C. for future use.

3. Preparation of responder cells (may contain mononuclear cells of activated lymphocytes to be tested): six months after heart transplantation (generally, regular test may be carried out 5 days after heart transplantation or when rejection is suspected to have occurred), 5-20 ml venous blood was drawn from recipients who have been testified by biopsy that no rejection occurred and recipients who have been testified by biopsy that first or third degree rejection occurred. In addition, 10 ml peripheral blood was drawn from normal individual who has never undergone transplantation. Mononuclear cells were prepared by the methods described above and used as responder cells which may contain donor antigen-specific activated lymphocyte; the mononuclear cells from normal individuals are used as responder cells, i.e. negative control which contains no donor antigen-specific activated lymphocyte (stimulator cell used in the experiment can be donor cells from any of the transplantation patients); the cells were washed twice by way of centrifuging with serum-free 1640 medium, and the precipitate was formulated into cell suspension with a concentration of $2 \times 10^6$ cells/ml by 1640 medium containing 0.125 ng FK506 (trade name Prograf, produced by Ireland Fujisawa Limited Company) and 5 µg methylprednisolone (produced by Belgium Pharmacia & Upjohn Company) per ml with 20% FCS (GIBCO company). The frozen donor spleen cells were thawed during the preparation of the responder cells. The cells were washed by serum-free 1640 medium at 1000 r/min. The precipitate was formulated into cell suspension with a concentration of $2 \times 10^6$ cells/ml by 1640 medium with 20% FCS and immunosuppressive agents, and used as stimulator cells (containing HLA antigens of donor) for future use.

4. Donor cells (stimulator cells), recipient cells (responder cells), and IL-2 N-mAb were seeded into a round-profile 96-well plate, the amounts of which used in each group are shown as below: Group A: 100 µl responder cells+100 µl stimulator cells; Group B: 100 µl responder cells+100 µl stimulator cells+15 µl IL-2 N-mAb; Group C: 100 µl responder cells+15 µl IL-2 N-mAb+100 µl 1640 medium used to dilute cells; Group D: 100 µl responder cells+100 µl 1640 medium used to dilute cells. Each group includes triplicate wells. Group B and Group C, which contain IL-2 N-mAb are the test group and control group in ALSA test, respectively. Group A and Group D, which contain no IL-2 N-mAb are the test group and control group in MLC test, respectively. The stimulator cells in negative control experiment can be donor cells from any of the heart transplantation patient, and the responder cells came from mononuclear cells in peripheral blood of normal individuals who have never received heart transplantation. After completing the above procedures, the cell culturing plate was incubated at 37° C. in $CO_2$ incubator.

5. The result from tetrazolium salt (MTT) colorimetry: 20 hours after cell culturing, 10 µl MTT was added in each well and kept in the incubator for another hour. The result was observed with reverse microscope to detect the amount of purple-blue formazan crystals converted from yellow soluble MTT in each well. Alternatively, tetrazolium salt (MTT) colorimetry can be used in the test: cell culture medium in each well was removed; then 150 µl Dimethyl Sulphoxide (DMSO) was added in each well and shaken gently for 5 minutes to dissolve the purple-blue crystals in the wells completely. Absorbance value at 550 nm in each well was measured with a microplate reader.

A. The direct observation results under inverted microscope are shown in FIGS. 1, 2, 3, and 4 (Markers A, B, C, and D in different Figures are consistent with group names in the Figure, for instance, A means group A)

Figure 1:
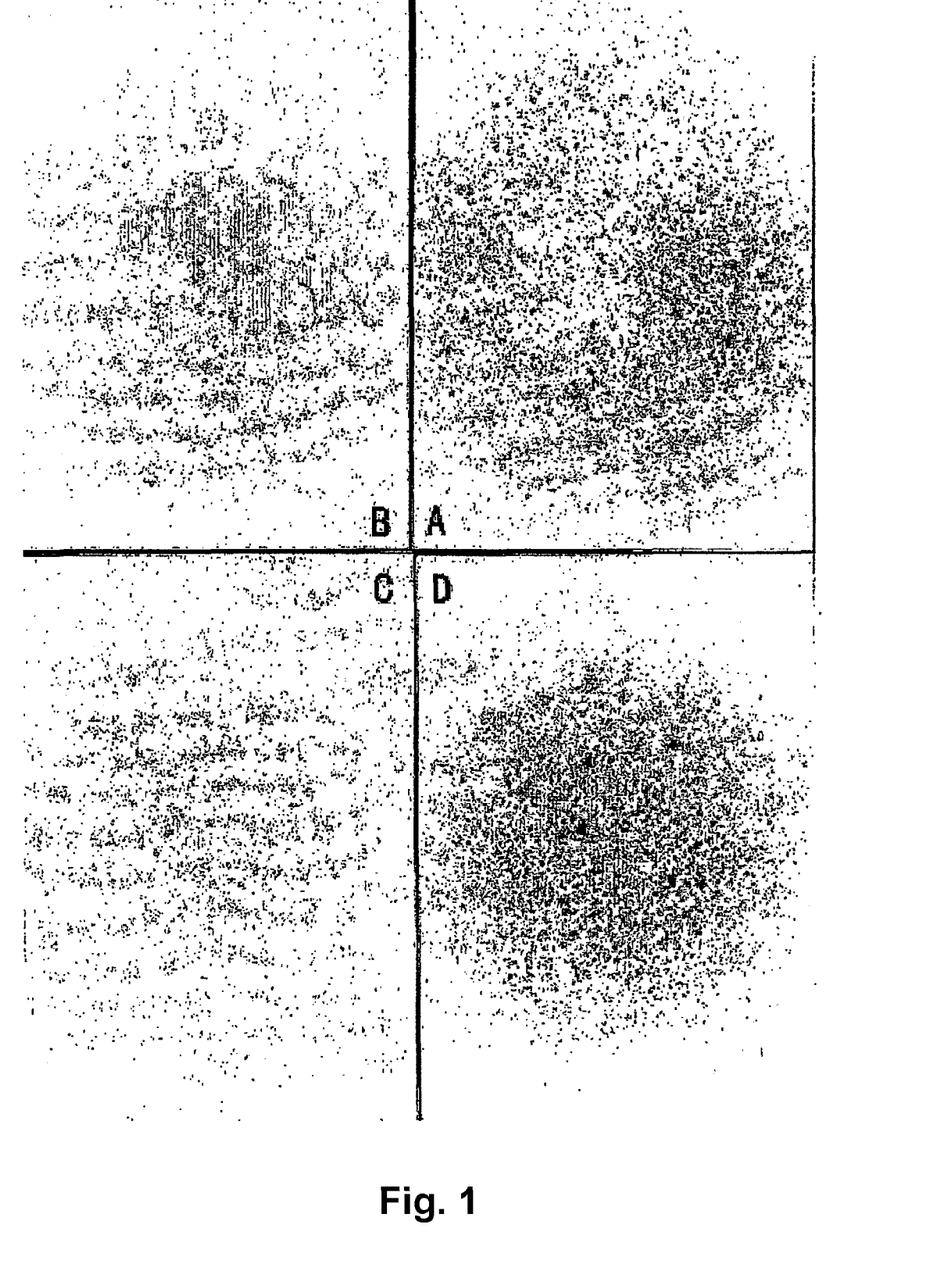
FIG. 1. Pictures showing ALSA test and MLC test results directly observed under inverted microscope (10×4), wherein the reaction (responder) cells came from normal person who has never experienced any organ transplantation; the experiment is negative control experiment (In reaction (responder) cells, no activated lymphocyte to any HLA antigens exists). The two pictures on the left side are testing results from ALSA experimental group (FIG. 1B) and control group (FIG. 1C); the two pictures on the right side are testing results from MLC experimental group (FIG. 1A) and control group (FIG. 1D).

FIG. 1 provided pictures show that ALSA test and MLC test results directly observed under inverted microscope (10×

4), wherein the reaction (responder) cells came from normal person who has never experienced any organ transplantation. As can be noticed from the pictures, there is no significant difference in results between ALSA test/experimental group (FIG. 1B) and control group (FIG. 1C). There is also no significant difference in results between MLC test group (FIG. 1A) and control group (FIG. 1D). All of these results indicate that there existed no activated lymphocyte corresponding to HLA antigens carried by stimulator cells. However, the cell activity of the control group in ALSA test is much weaker than that in the control group in MLC test, which indicates IL-2 N-mAb have inhibitory effect on cell activity.

Figure 2:
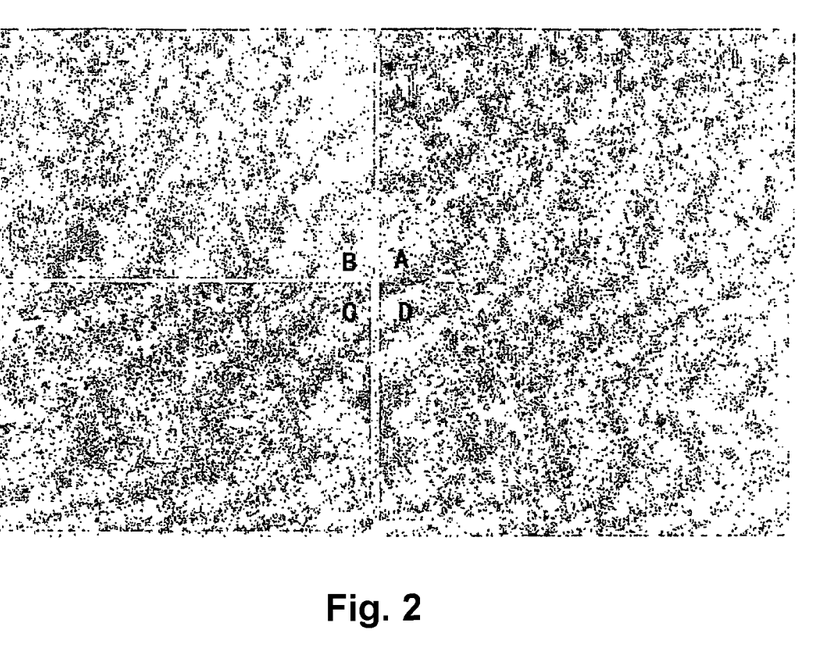
FIG. 2. Pictures showing ALSA test and MLC test results directly observed under inverted microscope (10×10), wherein the responder cells came from heart transplantation patients who have been proved by biopsy with no allograft rejection occurred. The two pictures on the left side are testing results from ALSA experimental group (FIG. 2B) and control group (FIG. 2C); the two pictures on the right side are testing results from MLC experimental group (FIG. 2A) and control group (FIG. 2D).

FIG. 2 provided pictures show that ALSA test and MLC test results directly observed under inverted microscope (10× 10), wherein the responder cells came from heart transplantation patients who have been proved by biopsy with no allograft rejection occurred. The result of the test group in ALSA test is not significantly weaker than that of control group, which indicates there existed no activated lymphocyte corresponding to HLA antigens carried by stimulator cells (donor cells) in reaction cells, i.e. no immunoreaction occurred (recipient did not attack donor cells). This result is consistent with biopsy result.

Figure 3:
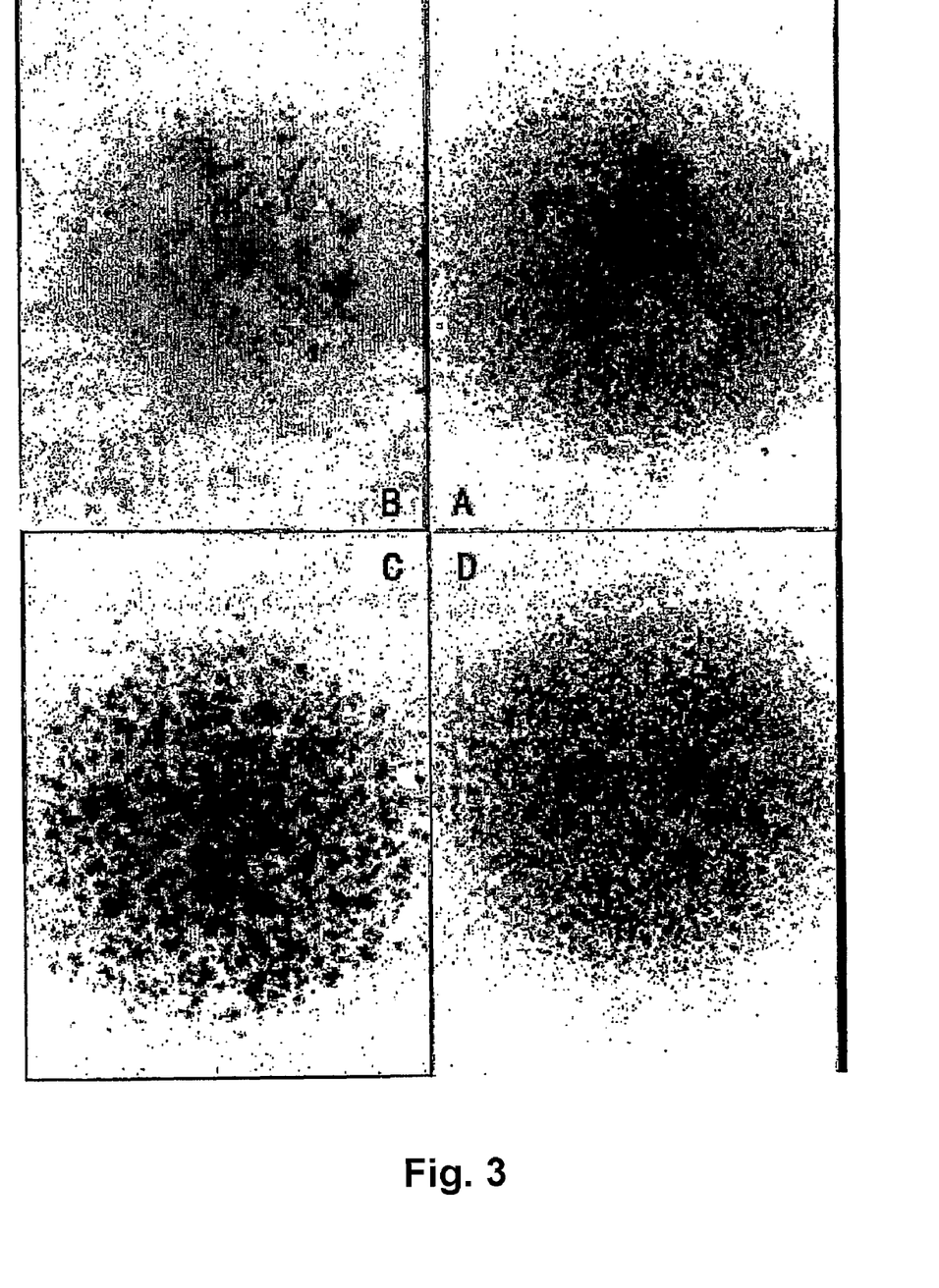
FIG. 3. Pictures showing ALSA test and MLC test results directly observed under inverted microscope (10×4), wherein the responder cells came from heart transplantation patients who have been proved by biopsy with first degree allograft rejection. The two pictures on the left side are testing results from ALSA experimental group (FIG. 3B) and control group (FIG. 3C); the two pictures on the right side are testing results from MLC experimental group (FIG. 3A) and control group (FIG. 3D).

FIG. 3 provided pictures show that ALSA test and MLC test results directly observed under inverted microscope (10× 4), wherein the responder cells came from heart transplantation patients who have been proved by biopsy with first degree allograft rejection. The two pictures on the left side are testing results from ALSA experimental group (FIG. 3B) and control group (FIG. 3C); the two pictures on the right side are testing results from MLC experimental group (FIG. 3A) and control group (FIG. 3D). The result of the test group in ALSA test is significantly weaker than that of control group, indicating there existed activated lymphocyte corresponding to HLA antigens carried by stimulator cells (donor cells) in reaction cells (recipient cells), i.e. immunoreaction occurred (recipient attacked donor cells). This result is consistent with biopsy result. However, there is no significant difference in the results between MLC test and control group, indicating MLC test is not an appropriate way to diagnose rejection during organ transplantation.

Figure 4:
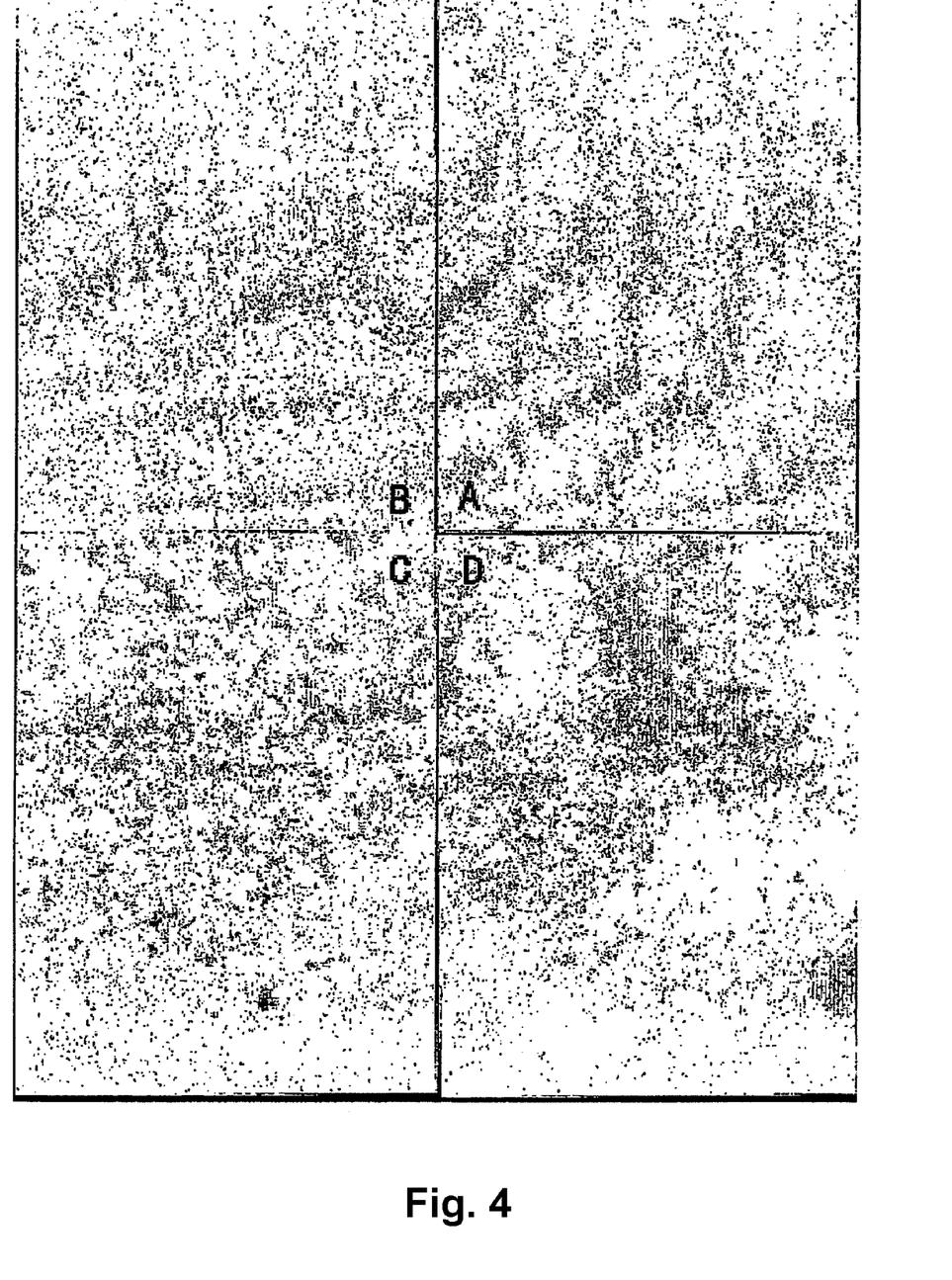
FIG. 4. Pictures showing ALSA test and MLC test results directly observed under inverted microscope (10×10), wherein the responder cells came from patients who have been proved by biopsy with third degree allograft rejection. The two pictures on the left side are testing results from ALSA experimental group (FIG. 4B) and control group (FIG.

FIG. 4 provided pictures show that ALSA test and MLC test results directly observed under inverted microscope (10× 10), wherein the responder cells came from patients who have been proved by biopsy with third degree allograft rejection. The two pictures on the left side are testing results from ALSA experimental group (FIG. 4B) and control group (FIG. 4C); the two pictures on the right side are testing results from MLC experimental group (FIG. 4A) and control group (FIG. 4D). As can be noticed from the pictures, the cell activity in the test group in ALSA test is totally inhibited (FIG. 4B). In contrast, cell activity in the control group is still relatively strong, indicating there existed activated lymphocyte corresponding to HLA antigens carried by stimulator cells (donor cells) in reaction cells (recipient cells), i.e. immunoreaction occurred (recipient attacked donor cells). Compared to control group, the cell activity in the test group in MLC test is much weaker (FIG. 4A). This may indicate there exists more activated lymphocyte corresponding to donor antigens in reaction cells, as this situation seldom happens during first degree rejection (see FIG. 3).

From the above results, as can be noticed, when rejection occurs, cell activity in the test group in ALSA test is much weaker than that in the control group (FIGS. 3B, 3C, 4B, and 4C). FIGS. 3B and 4B do not show the production of any formazan crystals, indicating there existed lymphocytes activated by HLA antigens expressed by donor cells in mononuclear cells of recipient, i.e. recipient has initiated immunoreaction against donor HLA antigens. The result from biopsy confirmed that primary and third degree rejection has occurred in patients. However, the results from test group and control group of MLC test sometimes have differences (FIGS. 4A and 4D), but sometimes not (FIGS. 3A and 3D), indicating MLC test is not an appropriate way to detect the existence of activated lymphocyte and diagnose rejection during organ transplantation.

When no rejection occurred, cell activities in the test group and control group of ALSA test may be weaker than those of MLC test (FIGS. 1B and 1C). However, there is no significant difference in cell activities between test group and control group in ALSA test (FIGS. 1B, 1C, 2B, and 2C).

Colorimetry: Other than direct observation under inverted microscope, the result of ALSA test can also be shown by chromometry. Cell culture medium in each well was removed; then 150 μl Dimethyl Sulphoxide (DMSO) was added in each well and shaken gently for 5 minutes to dissolve the formazan crystals in the wells completely. Absorbance value at 550 nm in each well was measured with a microplate reader.

Venous blood from recipient, who has been proven to have first degree rejection, was drawn to prepare lymphocyte to be tested. Procedures in 1-4 were repeated with different stimulator cell concentrations. The result of colorimetry is shown in Table 2.

TABLE 2

Reaction cells came from peripheral blood of recipients who have received heart transplantation and have been proved by biopsy to have first degree rejection; frozen-stored donor spleen cells thereof were used as stimulator cells; and the effects of different stimulator cell concentrations on ALSA and MLC tests were observed.

| Concentration of stimulator cells (/ml) | ALSA | | | MLC | | |
| --- | --- | --- | --- | --- | --- | --- |
| | Group B Test group | Group C Control group | Inhibitory rate (%) | Group A Test group | Group D Control group | Inhibitory rate (%) |
| $10^6$ | 0.135 | 0.223 | −39 | 0.389 | 0.304 | +28 |
| $10^5$ | 0.266 | 0.276 | −4 | 0.296 | 0.309 | −4 |
| $10^4$ | 0.221 | 0.266 | −17 | 0.426 | 0.385 | +11 |
| $10^3$ | 0.266 | 0.29 | −8 | 0.450 | 0.361 | +25 |

TABLE 2-continued

Reaction cells came from peripheral blood of recipients who have received heart transplantation and have been proved by biopsy to have first degree rejection; frozen-stored donor spleen cells thereof were used as stimulator cells; and the effects of different stimulator cell concentrations on ALSA and MLC tests were observed.

| Concentration of stimulator cells (/ml) | ALSA | | | MLC | | |
|---|---|---|---|---|---|---|
| | Group B Test group | Group C Control group | Inhibitory rate (%) | Group A Test group | Group D Control group | Inhibitory rate (%) |
| $10^2$ | 0.273 | 0.383 | −29 | 0.517 | 0.418 | +24 |
| $10^1$ | 0.355 | 0.275 | +29 | 0.456 | 0.400 | +14 |
| $10^0$ | 0.315 | 0.249 | +27 | 0.396 | 0.361 | +10 |

Note:
The note is same as in Table 1

Table 2 shows the result of the test group in ALSA test is significantly weaker than that of control group, indicating there existed lymphocytes activated by donor HLA antigens in reaction cells, i.e. recipient has initiated immunoreaction against donor organs. This result is consistent with biopsy result. The stimulator cell concentrations in ALSA test can be in the range of $10^6$-$10^2$/ml, i.e. all concentrations within this range can be used to test the existence of activated lymphocyte corresponding to antigens. A concentration below $10^2$/ml can not detect the existence of activated lymphocyte corresponding to antigens, as a result, it can not be used in rejection diagnosis. That is to say, during activated lymphocytes assay, the concentration of antigens to be tested should achieve a certain threshold to get accurate result, below which false negative may occur (see Table 2: the inconsistency of biopsy result with test results when using stimulation cells at concentrations of $10^1$/ml and $10^0$/ml, respectively). As it can be seen from Table 2, the inhibitory effects became the highest when using stimulator cells with concentrations of $10^6$ cells/ml and $10^2$ cells/ml, the results being −39% and −29% respectively. This further prove the conclusion from a reference (*Annu. Rev. Immunol.* 1999, 17:221-53) that too many or too less antigens may be favor of inducing the active apoptosis process of specific activated lymphocyte.

Venous blood from a recipient, who has been proved to have first degree rejection, was drawn to prepare lymphocyte to be tested. Procedures in 1-4 were repeated with different stimulator cell concentrations. The result of colorimetry is shown in Table 3.

TABLE 3

Reaction cells came from peripheral blood of recipients who have received heart transplantation and have been proved by biopsy with first degree rejection; frozen-stored donor spleen cells were used as stimulator cells; and the dynamic observation on different cell culture times in ALSA and MLC tests were provided.

| Cell culture time (h) | ALSA | | | MLC | | |
|---|---|---|---|---|---|---|
| | Group B Test group | Group C Control group | Inhibitory rate (%) | Group A Test group | Group D Control group | Inhibitory rate (%) |
| 1 | 0.137 | 0.124 | +10 | 0.310 | 0.192 | +61 |
| 2 | 0.071 | 0.09 | −21 | 0.153 | 0.109 | +40 |
| 3 | 0.113 | 0.114 | −1 | 0.240 | 0.160 | +50 |
| 4 | 0.039 | 0.062 | −37 | 0.150 | 0.162 | −7 |
| 5 | 0.058 | 0.156 | −63 | 0.270 | 0.232 | +16 |

TABLE 3-continued

Reaction cells came from peripheral blood of recipients who have received heart transplantation and have been proved by biopsy with first degree rejection; frozen-stored donor spleen cells were used as stimulator cells; and the dynamic observation on different cell culture times in ALSA and MLC tests were provided.

| Cell culture time (h) | ALSA | | | MLC | | |
|---|---|---|---|---|---|---|
| | Group B Test group | Group C Control group | Inhibitory rate (%) | Group A Test group | Group D Control group | Inhibitory rate (%) |
| 6 | 0.029 | 0.082 | −65 | 0.400 | 0.181 | +121 |
| 7 | 0.039 | 0.151 | −74 | 0.259 | 0.269 | −4 |
| 9 | 0.032 | 0.033 | −3 | 0.225 | 0.207 | +9 |
| 11 | 0.027 | 0.054 | −50 | 0.169 | 0.248 | −32 |
| 13 | 0.042 | 0.068 | −38 | 0.230 | 0.350 | −34 |
| 15 | 0.11 | 0.164 | −33 | 0.265 | 0.200 | +32 |
| 17 | 0.073 | 0.09 | −19 | 0.133 | 0.183 | −27 |
| 20 | 0.09 | 0.137 | −34 | 0.162 | 0.203 | −20 |

Note:
The note is same as in Table 1

The results of dynamic observation show the cell activities in test group in ALSA test is significantly weaker than that of control group after 2 hours of culturing, indicating there existed lymphocytes activated by donor HLA antigens in reaction cells (the present invention has so far described repetitively that when cell activities in test group in ALSA test is significantly weaker than that of control group, it indicates there exists specific lymphocytes activated by HLA antigens carried by stimulator cells in reaction cells), i.e. recipient has initiated immunoreaction against donor organs. This result is consistent with biopsy result. The highest inhibitory effect occurred 7 hours after cell culturing, with the inhibitory rate of 74%. The result also indicates ALSA test, when used in clinics, can achieve stable results after only two hours. Moreover, the results are further consistent with biopsy results. In contrast, the test results in MLC shown in Table 3 sometimes increase and sometimes decrease rather than having a stable outcome, further suggesting MLC should not be used in diagnosing activated lymphocytes.

Procedures in steps 1-4 were repeated to test individuals with different rejections, and the result of colorimetry is shown in Table 4. Groups marked with "*" indicate no immunosuppressive agent was used in ALSA and MLC test and the results were observed when MTT was added 72 hours after cell culturing.

Every heart transplantation patient was dynamically monitored, and the results were compared with pathological results obtained by biopsy.

TABLE 4

The comparison between ALSA and biopsy in different rejection grading

| | ALSA | | | MLC | | |
|---|---|---|---|---|---|---|
| Biopsy grading | Group B Test group | Group C Control group | Inhibitory rate (%) | Group A Test group | Group D Control group | Inhibitory rate (%) |
| Degree 3 | 0.02* | 0.098* | −80 | 0.118* | 0.122* | −3 |
| Degree 1 (primary) | 0.09 | 0.137 | −34 | 0.162 | 0.203 | −20 |
| Degree 1 | 0.135 | 0.223 | −39 | 0.389 | 0.304 | +28 |
| 0 | 0.263 | 0.287 | −8 | 0.374 | 0.328 | +14 |

As it can be noticed from the results in Table 4, the results of ALSA test are well consistent with those from biopsy test clinically. There may also exist connections between the gradings of biopsy rejections and the results from ALSA (inhibitory rate), i.e. the stronger the rejection, the higher the inhibitory rate.

Fifteen heart transplantation patients were monitored and tested by the present method for more than 100 times. Biopsy control was performed for 56 times. Positive results were obtained 29 times in the test, in which 18 cases have been proved by biopsy tests as no symptom rejection. Among the 18 cases, 4 cases were degree 3 rejection, 5 were II degree rejection, and nine were I degree rejection. Though the biopsy results of the other 11 positive cases indicated abnormality, the degree of the abnormality has not reached the diagnostic standard for degree 1 rejection. The biopsy test of 27 cases that were proved to be negative results by the present method are all negative.

TABLE 5

Consistency comparison between ALSA test and clinical biopsy test

| Test method | | Biopsy | |
|---|---|---|---|
| ALSA test | | Positive | Negative |
| | Positive | 18 | 11 |
| | negative | 0 | 27 |

The consistency, specificity, and sensitivity of the two test results are 80.3%, 71%, and 100%, respectively.

As can be seen from Table 1, 2, 3, and 4 and FIGS. 1, 2, 3, and 4, the results obtained by ALSA test are very objective, accurate, and unambiguous. Furthermore, ALSA test is simple, fast and easy to standardize.

As mentioned above, rejection starts as the activation of lymphocytes, therefore, activated lymphocytes should exist prior to pathological changes. The present invention lays particular emphasis on detecting the existence of donor antigen-specific activated lymphocytes in patients' peripheral blood. Accordingly, the rejection can be diagnosed by ALSA before pathological changes detected by biopsy. This can explain why there are "fake positive" cases in the test. Based on biopsy result, the 11 fake positive cases could not reach the diagnostic standard of degree 1 rejection, but this does not mean the patients are totally normal, on the contrary, this may be caused by the inadequate result of the biopsy test itself. That is to say, the relatively low specificity of the present method is due to its high sensitivity.

True positive (TP): ALSA test result indicates positive, and biopsy test result indicates rejection (≧I degree) occurred.

True negative (TN): ALSA test result indicates negative, and biopsy test result indicates no rejection occurred.

False positive (FP): ALSA test result indicates positive, but biopsy test result indicates no rejection occurred.

False negative (FN): ALSA test result indicates negative, but biopsy test result indicates rejection (≧I degree) occurred.

Consistency=(TP+TN)/(TP+TN+FP+FN)

Specificity=TN/(TN+FP)

Sensitivity=TP/(TP+FN)

According to the procedures described above and according to more than 1.00 times' ALSA and MLC tests results, as well as scores of biopsy results, the present invention concluded as follows the diagnostic standards used in rejection detection:

1. Direct Observation Under Inverted Microscope

| | |
|---|---|
| Rejection occurred | Cell activities in groups A (MLC test group) and B (ALSA test group) are significantly weaker than those in groups C (ALSA control group) and D (MLC control group). Especially in group B, the cell activity can be totally inhibited. The extent of weakening of cell activity in group A can be related to the degree of rejections. The higher the rejection degree, the lower the cell activity. When rejection degree is low, cell activity in group A is not significantly lower than that in groups in C and D. As long as rejection exists, cell activity in group B is significantly lower than that in groups in C, A, and D. |
| No rejection | There is no significant cell activity difference among all groups. Alternatively, cell activities in groups B and C are relatively weak. Sometimes cell activities in group C are even weaker. |
| No rejection occurred, the patient is currently or recently affected by bacteria or viruses, | Cell activities in all groups are relatively strong. There is no significant cell activity difference among all groups. Alternatively, cell activities in groups B and C are relatively weakened. |
| Rejection occurred, the patient is currently or recently affected by bacteria or viruses. | Cell activity in group A may be weakened. Cell activity in group B is significantly weaker than that in groups C, A, and D. Cell activity in group D is very strong, or cell activities in groups A, C, and D are all very strong. |

2. Measuring Absorbance Value in Each Well with Microplate Reader

A 10 µl MTT was added into each well 20 hours after cell culturing. The cell culture medium in each well was removed additional 0.5-1.5 hours later, then 150 µl Dimethyl Sulphoxide (DMSO) was added in each well and shaken gently for 5 minutes to dissolve the formazan crystals in the wells completely. Absorbance value at 550 nm in each well was measured with a microplate reader. Well containing no cells but 150 µl Dimethyl Sulphoxide (DMSO) was used as zero setting well. Using inhibitory rate as standard, positive was defined as more than 10% inhibition, and an inhibitory rate between 1 to 10% is defined as probable positive.

Example 3

The Diagnosis of Japanese B Encephalitis Virus Infected Patient

The preparation of Japanese B encephalitis virus-specific stimulator antigen: Purified Japanese B encephalitis virus was prepared by referring to *Journal of Medical Colleges of PLA* 1986, 1(4):356-362 and *Journal of Fourth Military Medical University* 1984 5(4): 251-254. The virus was fixed in 40 g/L formaldehyde at 4° C. overnight (about 12 hours) and then centrifuged and washed 4 times by normal saline. The protein content was assayed by ultraviolet spectrophotometer. The resultant antigens were divided into tubes, frozen-dried, and stored in refrigerator at −70° C.

The preparations of purified IL-2 N-mAb and tetrazolium (MTT) can be seen in Example 2.

The preparation of mononuclear cells to be tested: 5-10 ml venous blood was drawn from accurately diagnosed Japanese B encephalitis virus infected patients during high fever phase. Mononuclear cells were prepared using the method provided in Example 2. The cells were washed twice with serum-free 1640 medium, and the precipitate was formulated into cell suspension with a concentration of $2\times10^6$ cells/ml by 1640 medium (0.125 ng FK506 and 5 µg methylprednisolone per ml) with 20% FCS. The frozen Japanese B encephalitis virus were taken out and the viruses were formulated into virus protein suspension with a concentration of 3 mg/ml by 1640 medium (0.125 ng FK506 and 5 µg methylprednisolone per ml) with 20% FCS for future use.

Mononuclear cells, virus suspension, and IL-2 N-mAb were seeded into a round-profile 96-well plate, the amounts of which used in each group are shown below: Test group: 100 µl cells from patient to be tested+100 µl virus suspension+35 µl IL-2 N-mAb; Control group: 100 µl cells from patient to be tested+35 µl IL-2 N-mAb+100 µl 1640 medium used to dilute cells. Each group includes triplicate wells. After completing the above procedures, the cell culturing plate was incubated at 37° C. in $CO_2$ incubator.

MTT chromogenic method: 7 hours after cell culturing, 5 µl MTT was added in each well and kept in the incubator for another hour. Cell culture medium in each well was removed, then 100 µl Dimethyl Sulphoxide (DMSO) was added in each well and shaken gently for 5 minutes to dissolve the formazan crystals in the wells completely. Absorbance value in each well was measured with a microplate reader. The results can be seen in Table 6.

TABLE 6

The testing results of accurately diagnosed Japanese B encephalitis virus infected patients in high fever phase by ALSA method.

| | ALSA test | | |
|---|---|---|---|
| Cases | Test group | Control group | Inhibitory rate (%) |
| 1 | 0.167 | 0.469 | −64 |
| 2 | 0.254 | 0.482 | −47 |

Note:
Each value in test group and control group is the mean value of values in triplicate wells; inhibitory rate represents the extent of inhibition of Japanese B encephalitis virus antigen on specific activated lymphocyte; In ALSA test, each well was added with methylprednisolone and FK506, with the final concentration of 5 µg/ml and 0.125 ng/ml respectively.

As shown in the Table 6, the inhibitory effects of Japanese B encephalitis virus antigen to mononuclear cells reach 64% and 47%, respectively, indicating there existed plenty of activated lymphocyte corresponding to Japanese B encephalitis virus antigen in reaction cells, i.e. patients have been infected or vaccinated with Japanese B encephalitis virus recently.

What is claimed is:

1. A method for detecting antigen-specific, activated lymphocytes in an organism, comprising:
    exposing test lymphocytes from said organism to a target antigen in a medium for cell culture in the presence of neutralizing antibodies against cytokines which can induce cell proliferation, wherein the target antigen is selected from the group consisting of a human histocompatibility antigen, an allogeneic antigen, a heteroantigen, a viral antigen and a bacterial antigen;
    determining activity in said test lymphocytes and in control lymphocytes from said organism by measuring a detectable signal, wherein said control lymphocytes are exposed to an irrelevant antigen or no antigen in the presence of neutralizing antibodies against cytokines which can induce cell proliferation; and
    comparing activity of the test and control lymphocytes, wherein a lower activity of the test lymphocytes compared to the control lymphocytes is indicative of antigen-specific activated lymphocytes in the organism.

2. The method of claim 1, wherein the target antigen is a particulate antigen or soluble antigen; and wherein the human histocompatibility antigen is either one of the HLA type I or type II antigens, or a mixture of HLA type I antigen and HLA type II antigen.

3. The method of claim 1, further comprising adding an immunosuppressive agent and/or an anti-cancer medicament to said test and control lymphocytes, wherein the amount of the immunosuppressive agent or anti-cancer medicament is 0.001 ng-100 µg/ml medium and the amount of the cytokine neutralizing antibody is 1 µg-10 mg/ml medium.

4. The method of claim 1, wherein the detectable signal is measured by a method selected from the group consisting of MTT colorimetry, cell staining, fluorescent antigen staining and enzyme linked immunosorbent assay.

5. The method of claim 3, wherein the immunosuppressive agent is selected from the group consisting of Prograf (FK506), Cyclosporins, cyclophosphamide, azathioprine, rapamycin, RS-61443, BQR, immunosuppressant secreted by human acute T lymphocytic leukemia cell strain JM, deoxyspergualin, and adrenal cortex hormone, and wherein the anti-cancer medicament is selected from the group consisting of a topoisomerase inhibitor, an alkyling agent, an antimetabolite, and a derivative of retinoic acid-vitamin A.

6. The method of claim 5, wherein the immunosuppressive agent and the anti-cancer medicament are used alone or in combination.

7. The method of claim 5, wherein the adrenal cortex hormone is selected from the group consisting of medrat, prednisone, hydrocortisone and dexamethasone.

8. The method of claim 5, wherein the Cyclosporin is selected from the group consisting of Cyclosporin A and Cyclosporin C.

9. The method of claim 3, wherein the cytokines which can induce cell proliferation are selected from the group consisting of interleukin 1, 2, 3, 4, 5, 6, 7, 8, 9, 11, 12, 13, 14, 15, 16, 17, 18, 19, 20, 21, 22, and 23, α-interferon, β-interferon, ω-interferon, γ-interferon, granulocyte colony-stimulating factor, macrophage colony stimulating factor, granulocyte-macrophage colony stimulating factor, stem cell factor and thrombopoietin.

* * * * *